United States Patent [19]

Maguire

[11] Patent Number: 5,337,730
[45] Date of Patent: Aug. 16, 1994

[54] ENDOSCOPE CLEANSING CATHETER AND METHOD OF USE

[75] Inventor: Michael D. Maguire, St. Albans, Vt.

[73] Assignee: The United States of America as represented by the Secretary of the Air Force, Washington, D.C.

[21] Appl. No.: 900,404

[22] Filed: Jun. 18, 1992

[51] Int. Cl.⁵ .............................................. A61B 1/00
[52] U.S. Cl. .......................................... 128/4; 604/96; 604/267
[58] Field of Search .............................. 604/95–103, 604/267, 268; 606/7, 192–195; 128/4, 6, 5, 7–11

[56] References Cited

U.S. PATENT DOCUMENTS

| | | | |
|---|---|---|---|
| 1,852,351 | 4/1932 | Lewis | 604/96 |
| 2,470,665 | 5/1949 | Stiehl | 604/268 |
| 3,888,249 | 6/1975 | Spencer | 604/247 |
| 4,417,576 | 11/1983 | Baran | 604/101 |
| 4,423,725 | 1/1984 | Baran et al. | 604/101 |
| 4,445,892 | 5/1984 | Hussein et al. | 604/101 |
| 4,646,722 | 3/1987 | Silverstein et al. | 128/4 |
| 4,693,243 | 9/1987 | Buras | 604/96 |
| 4,765,314 | 8/1988 | Kolditz et al. | 128/4 |
| 4,793,326 | 12/1988 | Shishido | 128/4 |
| 4,836,187 | 6/1989 | Iwakoshi et al. | 128/4 |
| 4,841,952 | 6/1989 | Sato et al. | 128/4 |
| 4,844,052 | 7/1989 | Iwakoshi et al. | 128/4 |
| 4,862,874 | 9/1989 | Kellner | 128/6 |
| 4,947,827 | 8/1990 | Opie et al. | 128/4 |
| 4,950,278 | 8/1990 | Sachse et al. | 606/170 |
| 4,961,738 | 10/1990 | Mackin | 606/15 |
| 4,971,034 | 11/1990 | Doi et al. | 128/6 |
| 4,973,311 | 11/1990 | Iwakoshi et al. | 604/119 |
| 4,984,563 | 1/1991 | Renaud | 128/6 |
| 5,028,117 | 7/1991 | Muhlenkamp-Becker | 350/96.26 |
| 5,029,574 | 7/1991 | Shimamura et al. | 128/6 |
| 5,030,227 | 7/1991 | Rosenbluth et al. | 606/192 |
| 5,031,603 | 7/1991 | Gautier et al. | 128/4 |
| 5,049,132 | 9/1991 | Shaffer et al. | 604/101 |
| 5,176,638 | 1/1993 | Don Michael | 604/101 |

FOREIGN PATENT DOCUMENTS

| | | | |
|---|---|---|---|
| 1463310 | 3/1989 | U.S.S.R. | 604/99 |

*Primary Examiner*—C. Fred Rosenbaum
*Assistant Examiner*—Mark Bockelman
*Attorney, Agent, or Firm*—Fredric L. Sinder; Thomas L. Kundert

[57] ABSTRACT

A cleansing catheter for cleaning debris from the fiberoptic window ends of bronchoscopes, other endoscopes and the like, comprises a hollow catheter shaft (26) with an inflatable balloon (28) at one end. A preferred embodiment has a cylindrically shaped balloon (28) with a plurality of small holes (34) through the skin of the balloon arrayed about its annular base so that, when the balloon is filled with liquid, streams of liquid will escape through the holes back along the catheter shaft. In use, the cleansing catheter is advanced, with its balloon end collapsed, through a working channel of a bronchoscope or other endoscope until the balloon end just exits the working channel opening at the lens end of the endoscope. The balloon is then inflated with liquid delivered through the catheter shaft so that streams of liquid from the balloon holes spray against and clean debris from the fiberoptic window of the endoscope.

7 Claims, 2 Drawing Sheets

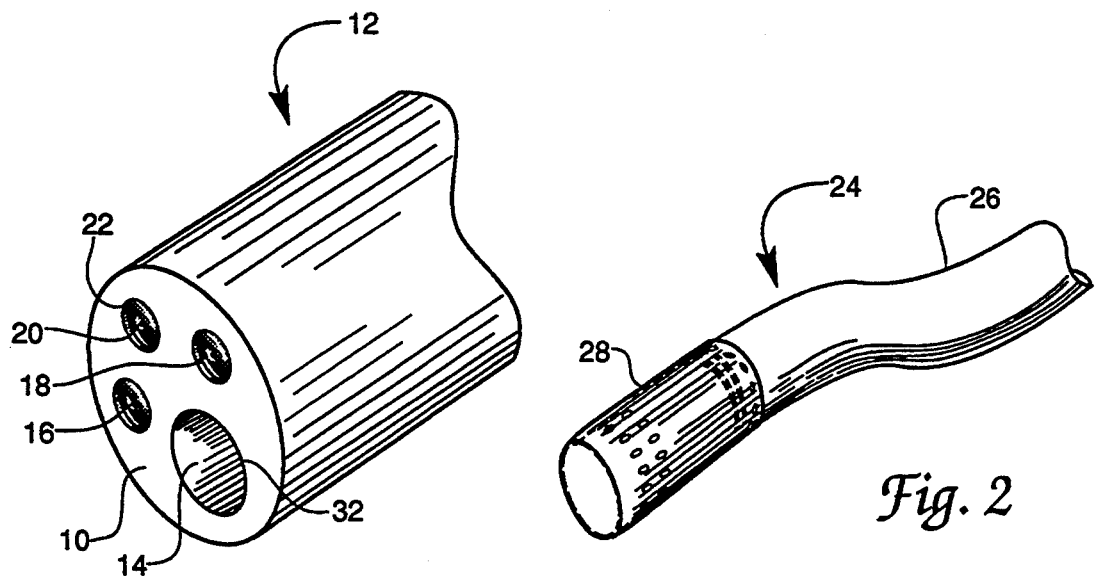
Fig. 1 Prior Art
Fig. 2
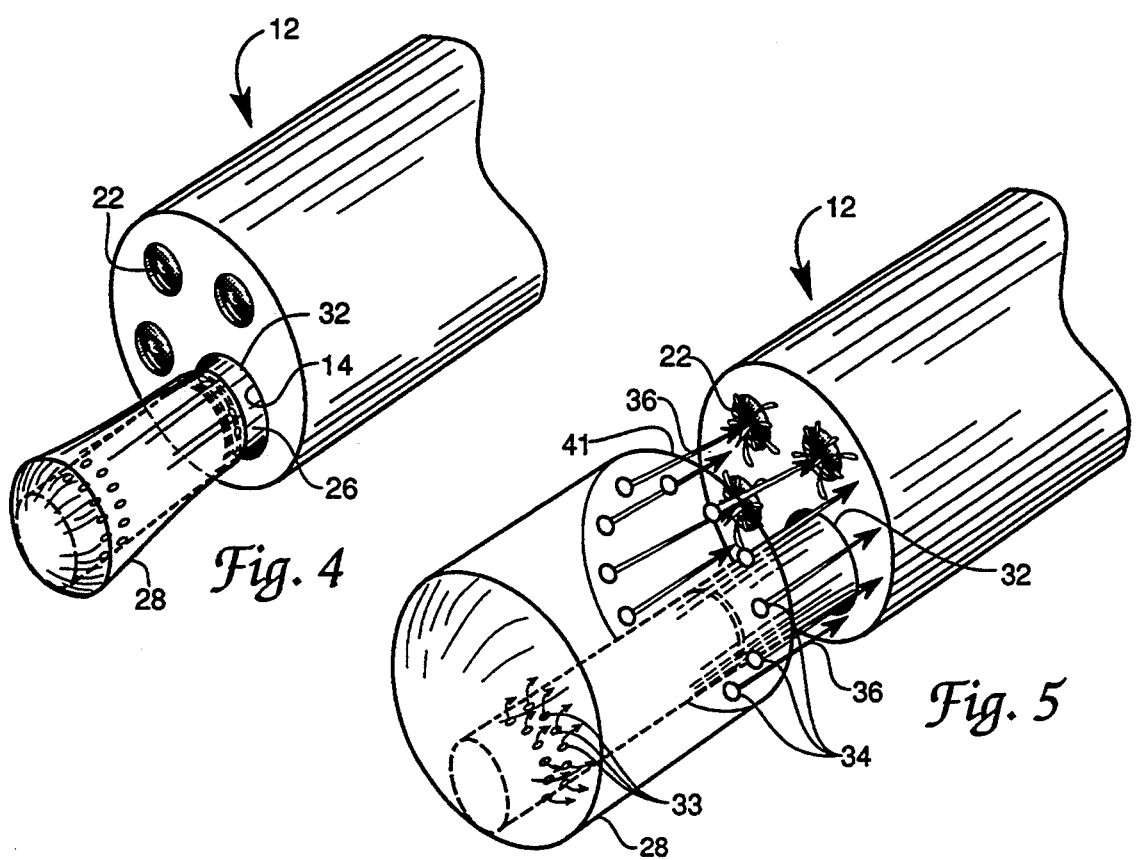
Fig. 4
Fig. 5

ENDOSCOPE CLEANSING CATHETER AND METHOD OF USE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to medical endoscopes, and more particularly to a catheter for cleaning the fiberoptic window end of a bronchoscope or any endoscope.

A bronchoscope is a flexible, steerable, fiberoptic equipped probe that is advanced into the lower respiratory tract for seeing inside ("visualizing") the respiratory tract. It is typically used for finding and collecting biopsy samples to determine the extent and etiology of respiratory disease, particularly cancer.

A typical bronchoscope has a single hollow channel or conduit (called a lumen, a biopsy channel or a working channel) throughout its length for passage of biopsy and other instruments; two fiberoptic channels for providing illumination; and, a single fiberoptic channel for visualization.

Other endoscopes may have different numbers of lumina and filled channels according to the needs of the particular medical procedures for which they are used.

Guiding a bronchoscope, or other endoscope, to a desired destination is a meticulous task, requiring frequent partial back ups and restarts and deft manipulation of the bronchoscope as it is fed into a body opening.

Unfortunately, the fiberoptic-window, located at the far, or lens end of the fiberoptic visualization channel, the end opposite from the eyepiece, frequently becomes coated with various bodily substances. This prevents visualization, thus disabling the bronchoscope and interrupting the procedure.

Past methods for cleaning debris from the fiberoptic window include the lavage method, in which the lens end of the bronchoscope is maneuvered so that it faces a body structure. A liquid is then rapidly injected through the biopsy channel or lumen to splash against the structure and try to reflect the splashed liquid back against the fiberoptic window surface to clean it.

Unfortunately, the lavage method is only occasionally successful, especially when blood clots soil the end of the bronchoscope. This technique is nearly impossible to use when the view through the bronchoscope is completely obstructed.

When a bronchoscope cannot be cleaned by the lavage or other prior art in vivo methods, the bronchoscope must be withdrawn to clean and its hard-earned positioning is then lost. Repositioning and revisualization of concerned structures is time consuming and intricate. It is painstakingly difficult to rediscover small and elusive lesions and tumors. Moreover, every time the bronchoscope is reinserted, dangerous reexposure to pathological microorganisms occurs, increasing the risk of infection and sepsic incidence. Consecutive reinsertions, or intubations, of the endoscope are progressively difficult and can also precipitate laryngospasm, a life threatening complication.

The endoscopic prior art includes a variety of apparatus and methods for cleaning soiled fiberoptic window surfaces. Typically, such apparatus is part of a separate outer sheath or other conduit that surrounds the endoscope either only at its lens end, or along its length. Such separate sheaths typically include a tube to deliver liquid to the sheath and ending in either a nozzle pointed back toward the fiberoptic window, or simply radially inwardly directed openings so that the fluid can clean the fiberoptic window when the endoscope is pulled back slightly within the sheath.

These prior art apparatus suffer from a number of deficiencies, not the least of which is that the sheaths or other endoscope surrounding apparatus add undesirable additional complexity and size to endoscopic probes.

Another problem with such sheaths is that they are typically too complex, and thus costly, to be made disposable. They are also difficult to clean and difficult to sterilize.

Thus it is seen that there is a need for an apparatus and method for cleaning endoscope fiberoptic windows in vivo without having to remove or reposition the endoscope.

It is, therefore, a principal object of the present invention to provide a simple and straightforward apparatus and method for cleaning endoscope fiberoptic windows in vivo without having to remove or reposition the endoscope.

It is a feature of the present invention that it will work, without requiring modification of either the invention or the endoscope, with any endoscope having an open channel.

It is another feature of the present invention that it can be easily made in a variety of different sizes using conventional catheter components to work with any size endoscope.

It is a further feature of the present invention that it can be made inexpensively and made disposable.

It is an advantage of the present invention that its use is fast, straightforward, easy and convenient.

It is another advantage of the present invention that it can be operated by feel and will work even when the view through the visualization channel is completely obstructed.

These and other objects, features and advantages of the present invention will become apparent as the description of certain representative embodiments proceeds.

SUMMARY OF THE INVENTION

The present invention provides a simple and effective apparatus and method for cleaning debris from the lens end of an endoscope without having to remove or reposition the endoscope. The unique discovery of the present invention is that the working, or any other open, channel present in nearly all endoscopes provides a means for inserting, and immediately thereafter removing, a specially designed catheter that can deliver a precisely directed stream of liquid to clean off the fiberoptic window of the endoscope. An additional unique discovery of the present invention is that a simple balloon catheter can be made with an inflatable balloon at its far end in which the balloon has one or more small holes arrayed at or near its back so that, when the balloon is pushed just past the open lens end of an endoscope and inflated with a liquid, the liquid will spray back toward the endoscope to clean its fiberoptic window.

Another unique discovery of the present invention is that the balloon is preferably made of a less elastic material in the shape of a cylinder so that, as it is inflated with a liquid, the small holes at its base do not significantly change the direction in which they spray the liquid.

Accordingly, the present invention is directed to a cleansing catheter for cleaning the lens end of an endoscope, comprising a hollow catheter shaft having an end, an inflatable balloon at the end of the catheter shaft, wherein the balloon has a skin; and, one or more openings through the skin of the balloon positioned so that, when the balloon is inflated with a fluid, the fluid is directed under pressure in a preselected direction. The one or more openings may be positioned so that the fluid is directed under pressure in a direction back along the catheter shaft. The balloon may have a generally cylindrical shape when inflated. The generally cylindrical balloon may have an annular base, wherein the one or more openings are positioned along that annular base so that the fluid is directed under pressure in a direction back along the catheter shaft. The balloon may also have a generally spherical shape when inflated. The generally spherical balloon may have a neck, wherein the one or more openings are arrayed around the neck of the balloon so that the fluid is directed under pressure in a direction back along the catheter shaft.

The invention is also directed to a method for cleaning the lens end of an endoscope, comprising the steps of providing a cleansing catheter as described, passing the cleansing catheter through a channel inside the endoscope until the balloon emerges from the lens end of the endoscope; and, inflating the balloon with a fluid delivered to the balloon through the catheter shaft so that the fluid is directed back toward the lens end of the endoscope. The method may further comprise the step of determining when the balloon has emerged from the lens end of the endoscope by detecting for a reduction in back pressure of the fluid inside the catheter shaft.

DESCRIPTION OF THE DRAWINGS

The present invention will be more clearly understood from a reading of the following detailed description in conjunction with the accompanying drawings wherein:

FIG. 1 is a representative perspective view of the lens end of a prior art bronchoscope or other endoscope;

FIG. 2 is a representative perspective view of a preferred embodiment of a cleansing catheter made according to the teachings of the present invention showing a generally cylindrical balloon end in a deflated condition;

FIG. 4 is a representative perspective view of the cleansing catheter of FIG. 2 being advanced past the working channel opening of the bronchoscope of FIG. 1;

FIG. 5 is a representative perspective view of the cleansing catheter of FIG. 2 having its balloon end positioned just ahead of the bronchoscope and inflated with a liquid so that it sprays the liquid back toward to the bronchoscope to clean its lens end; and, FIG. 6 is a representative perspective view of the cleansing catheter of FIG. 3 having its balloon end positioned just ahead of the bronchoscope and inflated with a liquid so that it sprays the liquid back toward the bronchoscope to clean its lens end.

DETAILED DESCRIPTION

Figure 3:
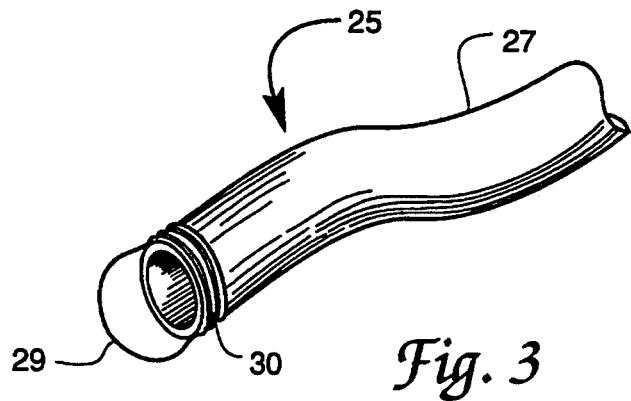
FIG. 3 is a representative perspective view of another embodiment of a cleansing catheter made according to the teachings of the present invention showing a generally spherical balloon end in a mostly deflated condition.

Referring now to FIG. 1 of the drawings, there is shown a representative perspective view of the lens end 10 of a prior art bronchoscope, or other endoscope, 12. Bronchoscope 12 includes a working or biopsy channel (also called a lumina) 14, two fiberoptic illumination channels 16 and 18, and a single fiberoptic visualization channel 20. The outside surface 22 of fiberoptic visualization channel 20 can be referred to as fiberoptic window 22.

The use of bronchoscope 12 is well-known in the art. Very briefly, it is guided from its eyepiece or handle end through the nose, sinus passages and throat of a patient to the patient's lower respiratory tract. As it is guided, its path is viewed through visualization channel 20 and illumination is provided from illumination channels 16 and 18. Working channel 14 may be used to deliver streams of liquid to clear away debris from respiratory surfaces, to provide passage for a forceps to take a biopsy sample, or for a variety of other uses.

FIG. 2 is a representative perspective view of a preferred embodiment of a cleansing catheter 24 made according to the teachings of the present invention. Catheter 24 includes a flexible single lumen catheter shaft 26 and a cylindrical balloon 28. Cylindrical balloon 28 is shown in a deflated condition in this Figure. Cleansing catheter 24 is about 60 cm long and 3 mm in diameter. Balloon 28 is about 8 mm long and about 8 mm in diameter when fully inflated. Catheter shaft 26 is constructed to withstand considerable torques. The outside or handle end (not shown) of cleansing catheter 24 has a standard leuer-lock interface for connection to various size syringes. A swivel connection should preferably be added so that catheter 24 can be more easily rotated.

FIG. 3 is a representative perspective view of another embodiment of a cleansing catheter 25 made according to the teachings of the present invention. Catheter 25 also includes a flexible single lumen catheter shaft 27 similar to catheter shaft 26 and a spherical balloon 29. Spherical balloon 29 is shown in a mostly deflated position in FIG. 2. Spherical balloon 29 includes a neck 30 where balloon 29 attaches to catheter shaft 27. The attachment may be by separate attachment means, or balloon 29 may be more integrated as part of catheter shaft 27.

FIG. 4 is a representative perspective view of cleansing catheter 24 being advanced or pushed through working channel 14 and past its opening 32. Cylindrical balloon 28 is filled with pressurized fluid, but is prevented from inflating by the inner walls of working channel 14.

FIG. 5 shows balloon 28 of cleansing catheter 24 now inflated and positioned slightly in front of opening 32. Balloon 28 is inflated by water or saline solution delivered to it through hollow catheter shaft 26. A plurality of small holes 34 through the skin of balloon 28 can now be better seen arrayed about its annular base 41. The end of catheter shaft 26 preferably butts against the end of balloon 28 and is preferably sealed. A plurality of holes 33 circle catheter shaft 26 near its end. Streams 36 of liquid are forced under pressure through holes 33 and then through holes 34 to spray back onto fiberoptic window 22 and wash off any debris. The orientation of holes 33 and 34 facilitate the flow toward fiberoptic window 22. Streams 36 of liquid do not have to be well aimed at fiberoptic window 22. Small operator initiated back-and-forth movements and rotations of cleansing catheter 24 will cause different streams 36 to sweep back and forth across fiberoptic window 22. Balloon 28 can even be pulled against fiberoptic window to mechanically agitate difficult deposits while streams 36 both help the agitation and wash away debris. Once vision is restored and a stream 36 can be seen impinging on fiberoptic window 22, cleansing catheter 24 can then be even more finely controlled to complete cleaning. After cleaning is finished, the liquid pressure is released and balloon 28 and catheter shaft 26 removed so that working channel 14 is then free for other work.

Pressurizing the liquid inside cleansing catheter 24, typically from a syringe mounted at the handle end of cleansing catheter 24, is begun before balloon 28 exits through opening 32. The operator will feel a slight back pressure through the syringe plunger while balloon 28 is still inside working channel 14. The operator will feel a reduction of the back pressure as balloon 28 exits opening 32 and begins to inflate. It may be necessary to pull back slightly on catheter shaft 26 immediately after the back pressure drops to position holes 34 at an optimum distance from fiberoptic window 32. The operator will know when balloon 28 has been pulled too far back because it will strike the end 10 of endoscope 12. The operator can, therefore, position balloon 28 and perform the cleaning operation by feel without having to be able to see the balloon and without the hit and miss approach often required by searching for a suitable structure in performing the lavage method.

Catheter shaft 26 has a single large lumen to deliver the maximum possible volume of fluid to balloon 28 so that streams 36 of fluid are as powerful as possible. Balloon 28 may be a separate structure attached to catheter shaft 26 or may be an integrated extension from shaft 26. Holes 36 may be arrayed in a variety of patterns according to the relative positions of balloon 28 and the fiberoptic window 22 of a particular endoscope. They typically will be located surrounding the neck portion of the balloon so that fluid stream 36 is directed back along catheter shaft 26 to most readily strike the end of an endoscope where fiberoptic window is typically located. While typically the same type syringe and liquid used with the endoscope working channel will be used with cleansing catheter 24, other liquids more specifically useful for cleaning may be used. The term "fluid" as used in the claims is intended to include any suitable fluid, such as liquids, gases, bubble-filled liquids, slurries and so forth.

Figure 6:
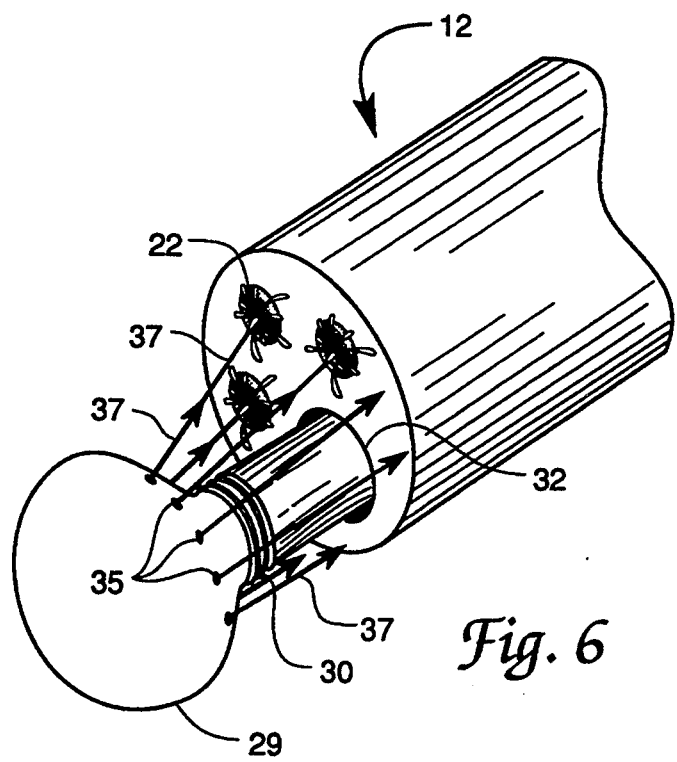

FIG. 6 shows spherical balloon 29 of FIG. 3 now also inflated by water or saline solution and positioned slightly in front of opening 32. A plurality of small holes 35 can now be seen arrayed about balloon neck 30. Similarly to the operation of cylindrical balloon 28, streams 37 of liquid are forced under pressure through holes 34 to spray back onto fiberoptic window 22 and wash off any debris.

A problem discovered with using spherical balloons 29 made of highly elastic material is that as the balloons expand, holes 35 move so that the streams of liquid begin to point in a direction away from the axis of the cleansing catheter, and no longer back toward fiberoptic window 22. To prevent that problem, cylindrical balloon 8 should not only be made in a cylindrical shape having its holes arrayed about its base, but also should preferably be made of a less elastic material so that it will better retain its shape and not expand so much as to allow holes 34, and the direction of streams 36, to significantly move. Cylindrical balloon 28 does not have to be tightly elastically contracted around the end of catheter shaft 26 in its deflated condition. It needs only be sufficiently contracted to fit easily through working channel 14.

The disclosed cleansing catheter successfully demonstrates modifying preexisting surgical or invasive procedure device components to perform new functions and further to combine the modified components in new ways to achieve new useful results. Although the disclosed apparatus is specialized, its teachings will find application in other areas where there exists a number of preexisting components capable of being modified and combined in nonobvious ways to solve existing problems.

Those with skill in the art of the invention will readily see modifications that may be made to the disclosed cleansing catheter. For example, the balloon may be made in a variety of other inflated shapes to, for example, provide a skirt around its base to better focus the backward spray. The balloon may also include rearward projections so that, when pulled back slightly after exiting from an endoscope working channel, the rearward projections agitate, or brush, the end of the endoscope. The projections may be made of different material, including brush-like material.

A further modification that can be made is to make the holes smaller, fewer, or along a single side to increase the velocity of the streams for more efficient cleaning.

It is understood that various other modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

I claim:

1. A combination endoscope and cleansing catheter for cleaning the lens of the endoscope, comprising;
   (a) an endoscope having a lens end;
   (b) a hollow catheter shaft having an end;
   (c) an inflatable balloon attached at the end of the catheter shaft, wherein the balloon has a skin;
   (d) one or more openings through the skin of the balloon positioned so that, when the balloon is inflated with a fluid delivered through the inside of the catheter shaft, the fluid is directed under pressure only in a direction backward along the catheter shaft; and wherein the rest of the skin of the balloon is free of openings.

2. The combination endoscope and cleansing catheter according to claim 1, wherein the balloon has a generally cylindrical shape when inflated.

3. The combination endoscope and cleansing catheter according to claim 2, wherein the generally cylindrical balloon has an annular base, and wherein the one or more openings are positioned along that annular base so that the fluid is directed under pressure in a direction back along the catheter shaft.

4. The combination endoscope and cleansing catheter according to claim 1, wherein the balloon has a generally spherical shape when inflated.

5. The combination endoscope and cleansing catheter according to claim 4, wherein the generally spherical balloon has a neck, and wherein the one or more openings are arrayed around the neck of the balloon so that the fluid is directed under pressure in a direction back along the catheter shaft.

6. A method for cleaning the lens end of an endoscope, comprising the steps of:
   (a) providing a cleansing catheter, comprising:
      (i) a hollow catheter shaft having an end;
      (ii) an inflatable balloon attached at the end of the catheter shaft, wherein the balloon has a skin; and,
      (iii) one or more openings through the skin of the balloon positioned so that, when the balloon is inflated with a fluid delivered through the inside of the catheter shaft, the fluid is directed under pressure only backward along the catheter shaft;
   (b) passing the cleansing catheter through a channel inside the endoscope until the balloon emerges from the lens end of the endoscope;
   (c) inflating the balloon with a fluid delivered to the balloon through the catheter shaft so that the fluid is directed only backward toward the lens end of the endoscope; and,
   (d) sweeping the fluid across the lens end of the endoscope to clean that lens end.

7. The method for cleansing the end of an endoscope according to claim 6, further comprising the step of determining when the balloon has emerged from the lens end of the endoscope by feeling for a reduction in back pressure of the fluid inside the catheter shaft.

* * * * *